(12) United States Patent
Jones

(10) Patent No.: US 12,102,656 B2
(45) Date of Patent: Oct. 1, 2024

(54) TOPICAL COMPOSITIONS INCORPORATING CANNABIS

(71) Applicant: DONA J LLC, San Diego, CA (US)

(72) Inventor: Lisa Marie Jones, San Diego, CA (US)

(73) Assignee: Dona J LLC, San Diego, CA (US)

( * ) Notice: Subject to any disclaimer, the term of this patent is extended or adjusted under 35 U.S.C. 154(b) by 778 days.

(21) Appl. No.: 17/232,620

(22) Filed: Apr. 16, 2021

(65) Prior Publication Data

US 2021/0252088 A1    Aug. 19, 2021

Related U.S. Application Data

(63) Continuation of application No. PCT/US2019/055654, filed on Oct. 10, 2019.

(60) Provisional application No. 62/748,967, filed on Oct. 22, 2018.

(51) Int. Cl.
| | | |
|---|---|---|
| A61K 36/185 | (2006.01) |
| A61K 9/00 | (2006.01) |
| A61K 9/06 | (2006.01) |
| A61K 47/44 | (2017.01) |
| A61K 47/46 | (2006.01) |

(52) U.S. Cl.
CPC .......... *A61K 36/185* (2013.01); *A61K 9/0014* (2013.01); *A61K 9/06* (2013.01); *A61K 47/44* (2013.01); *A61K 47/46* (2013.01); *A61K 2236/31* (2013.01); *A61K 2236/35* (2013.01); *A61K 2236/37* (2013.01); *A61K 2236/53* (2013.01)

(58) Field of Classification Search
None
See application file for complete search history.

(56) References Cited

U.S. PATENT DOCUMENTS

| 6,949,582 B1 | 9/2005 | Wallace |
| 8,425,950 B1 | 4/2013 | Santillan et al. |
| 8,425,954 B2 | 4/2013 | Stone |
| 9,078,838 B2 | 7/2015 | Andre et al. |
| 9,095,563 B2 | 8/2015 | Sekura et al. |
| 2012/0095087 A1 | 4/2012 | Hyatt |
| 2012/0264818 A1 | 10/2012 | Newland |
| 2013/0184354 A1 | 7/2013 | Jackson et al. |
| 2013/0274321 A1 | 10/2013 | Newland |
| 2014/0302185 A1 | 10/2014 | Cavalieri Manasse |
| 2015/0290267 A1 | 10/2015 | Sekura et al. |
| 2016/0287652 A1 | 10/2016 | Scott |
| 2017/0143781 A1 | 5/2017 | Yarborough |
| 2018/0042890 A1 | 2/2018 | Sinai et al. |

FOREIGN PATENT DOCUMENTS

| CA | 3 049 489 A1 | 7/2018 |
| WO | WO 2010/150245 A1 | 12/2010 |
| WO | WO 2015/142574 A1 | 9/2015 |
| WO | WO 2017/037534 A1 | 3/2017 |
| WO | WO 2017/055846 A1 | 4/2017 |
| WO | WO 2017/175126 A1 | 10/2017 |
| WO | WO 2018/023164 A1 | 2/2018 |
| WO | WO 2018/061009 A1 | 4/2018 |

OTHER PUBLICATIONS

International Search Report and Written Opinion dated Dec. 6, 2019 for Application No. PCT/US2019/055654.
Leafly Staff) What is kief and how can you use it?. Jul. 6, 2017; https://www.leafly.com/news/cannabis-101/what-is-kief; retrieved from the internet: Nov. 20, 2019: p. 8, second paragraph.

*Primary Examiner* — Michael V Meller
(74) *Attorney, Agent, or Firm* — Knobbe, Martens, Olson & Bear, LLP

(57) ABSTRACT

Topical formulations containing cannabis are provided. A formulation may include a cannabis flower extract, an emollient, a plant extract such as lavender flower or chamomile flower, and one or more excipients. Methods of making and methods of using topical formulations are also provided.

8 Claims, No Drawings

TOPICAL COMPOSITIONS INCORPORATING CANNABIS

CROSS REFERENCE TO RELATED APPLICATIONS

This application is a continuation of International Application No. PCT/US2019/055654, filed on Oct. 10, 2019 and published on Apr. 30, 2020 as WO 2020/086291, which claims the benefit of U.S. Provisional Application No. 62/748,967, filed on Oct. 22, 2018.

FIELD

The present disclosure relates generally to the field of topical compositions, including compositions for the treatment and improvement of skin conditions. In particular, the disclosure relates to topical compositions incorporating cannabis-derived compounds.

BACKGROUND

The botanical genus cannabis represents a group of plants that produce chemicals known as cannabinoids. Among the cannabinoids are tetrahydrocannabinol (THC) and cannabidiol (CBD), in addition to numerous other natural substances. These compounds have been reported to have numerous benefits, including analgesic, anti-inflammatory, antibiotic, and anti-oxidant activity.

Cannabis also has a long history of use for hemp fiber, hemp oils, medicinal purposes, and as a recreational drug. Incorporating cannabinoids in topical formulations will provide users with a way to experience the benefits of these compounds on the skin.

SUMMARY

In one aspect, a formulation is disclosed that includes, for example, an emollient selected from the group including shea butter, cocoa butter, or a combination thereof, the emollient present in an amount greater than or equal to about 50% by volume, an oil, a cannabis flower extract, a plant extract selected from the group including lavender flower, chamomile flower, or a combination thereof, and one or more excipients.

In some embodiments, the formulation is a topical formulation. In some embodiments, the emollient is present in an amount between about 50% and about 90% by volume. In some embodiments, the emollient is present in an amount of about 80% by volume.

In some embodiments, the oil is present in an amount between about 5% and about 20% by volume. In some embodiments, the oil is present in an amount of about 10% by volume. In some embodiments, the oil is almond oil.

In some embodiments, the cannabis flower extract is present in an amount of about 0.01% to about 2% by volume. In some embodiments, the plant extract is present in an amount of about 0.01% to about 2% by volume.

In some embodiments, the one or more excipients are present in an amount of about 5% to about 20% by volume. In some embodiments, the one or more excipients are present in an amount of about 10% by volume. In some embodiments, the excipients are selected from the group consisting of tea tree oil and *arnica* oil.

In another aspect, a formulation is disclosed that includes, for example, an emollient selected from the group including shea butter, cocoa butter, or a combination thereof, the emollient present in an amount greater than or equal to about 50% by volume, an oil, a kief extract, and a plant extract selected from the group including chamomile, lavender, *arnica*, tea tree, or a combination thereof.

In some embodiments, the formulation is a topical formulation. In some embodiments, the emollient is present in an amount of about 50% to about 90% by volume. In some embodiments, the emollient is present in an amount of about 80% by volume.

In some embodiments, the oil is present in an amount of about 5% to about 20% by volume. In some embodiments, the oil is present in an amount of about 9% by volume. In some embodiments, the oil is almond oil.

In some embodiments, the kief extract is present in an amount of about 0.01% to about 2% by volume. In some embodiments, the plant extract is present in an amount of about 0.01% to about 2% by volume.

A method for manufacturing a topical composition is also disclosed herein. The method includes, for example, combining cannabis flower and an oil to create a first mixture, heating the first mixture to a temperature within the range of about 250° C. to about 300° C. for approximately one to three hours, removing solids from the first mixture by filtration, and combining the filtrate with shea butter, cocoa butter, or a combination thereof to create a second mixture.

In some embodiments, the oil is almond oil. In some embodiments, the first mixture is heated to a temperature of about 260° C. In some embodiments, the first mixture is heated for approximately two hours. In some embodiments, the filtration is carried out with a paper filter.

DETAILED DESCRIPTION

Embodiments provided herein relate to topical formulations comprising cannabis-derived compounds. The compositions may be provided to a subject for topical application to skin.

It will be readily understood that the aspects of the present disclosure, as generally described herein, can be arranged, substituted, combined, separated, and designed in a wide variety of different configurations, all of which are explicitly contemplated herein.

Definitions

Unless defined otherwise, technical and scientific terms used herein have the same meaning as commonly understood by one of ordinary skill in the art to which the present disclosure belongs.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, a "subject" or a "patient" refers to an animal that is the object of treatment, observation or experiment. "Animal" comprises cold- and warm-blooded vertebrates and invertebrates such as fish, shellfish, reptiles and, in particular, mammals. "Mammal" comprises, without limitation, mice, rats, rabbits, guinea pigs, dogs, cats, sheep, goats, cows, horses, primates, such as monkeys, chimpanzees, and apes, and, in particular, humans. In some alternatives, the subject is human.

Some embodiments disclosed herein relate to selecting a subject or patient in need. In some embodiments, a patient is selected who is in need of treatment, amelioration, inhibition, progression, prophylaxis, or improvement in disease symptoms or who is in need of curative therapy.

As used herein, the term "treatment" refers to an intervention made in response to a disease, disorder, or physiological condition manifested by a subject. The terms treating, treatment, therapeutic, or therapy do not necessarily mean total cure or abolition of the disease or condition. For example, in some embodiments, treatments reduce, alleviate, ameliorate, or eradicate the symptom(s) of the disease and/or provide curative therapy of the disease.

The term "therapeutically effective amount" is used to indicate an amount of a composition that elicits the biological or medicinal response indicated. Determination of a therapeutically effective amount is within the capability of those skilled in the art, in view of the disclosure provided herein. The therapeutically effective amount of the composition disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As used herein, an "emollient" refers to a compound that soothes the skin. In some embodiments, an emollient is a moisturizer, a cream, a lotion, an oil, a rub, a salve, or a balm. In some embodiments, the emollient is a moisturizer. In some embodiments, the moisturizer is shea butter or cocoa butter. Shea butter is a fat extracted from the nut of the shea tree. Cocoa butter is a fat extracted from the cocoa bean. In some embodiments, the moisturizer is olive oil, coconut oil, avocado oil, dimethicone, petroleum jelly, glycerin, ceramide, honey, buttermilk, castor oil, aloe, aloe butter, argan oil, flaxseed oil, jojoba oil, rose hip seed oil, safflower oil, sunflower oil, mango butter, kokum butter, almond butter, apricot kernel butter, hemp butter, macadamia nut butter, sal butter, beeswax, black cumin seed oil, and vitamin E oil.

As used herein, a "plant extract" is a component of group of components removed from one or more plants. In some embodiments, the plant is lavender, chamomile, arnica, tea tree, basil, black pepper, cardamom, blue tansy, cassia, bergamot, cedar, cilantro, cinnamon, clary sage, clove, coriander, cypress, Douglas fir, frankincense, melaleuca, oregano, peppermint, eucalyptus, fennel, geranium, ginger, grapefruit, jasmine, juniper berry, lemon, lemongrass, lime, marjoram, myrrh, patchouli, rose, rosemary, sandalwood, Siberian fir, spearmint, tangerine, thyme, orange, wintergreen, and ylang-ylang. In some embodiments, the plant is cumin, rosehip, grapeseed, licorice, almond, green tea, witch-hazel, and pomegranate.

As used herein, "tea tree oil" is an essential oil derived from the leaves of the tea tree. As used herein, "arnica oil" is an essential oil derived from the flower heads of plants in the arnica genus.

As used herein, a "cannabis flower extract" is a component or group of components removed from the flowering portion of cannabis plants.

As used herein, a "kief extract" is a component or group of components removed from kief.

As used herein, an "excipient" is a substance formulated alongside the other ingredients, included for the purpose of improving stabilization of the composition, bulking up the composition, or to confer an enhancement on the effects of one or more other ingredients in the composition. An excipient may be an adherent, a binder, a coating, a color, a disintegrant, a flavor, a glidant, a lubricant, a preservative, a sorbent, a sweetener, or a vehicle.

The formulations provided herein may be prepared, packaged, or sold for topical administration. The formulations can be filled into suitable packaging (containers) such as, for example, tubes, cartons, capsule, jars, bottles, canisters, squeeze pack, pouches, packages, packets, sacks, tank, or other containers. In some embodiments, the formulation may be applied directly to skin. In some embodiments, the formulation may be applied an applicator, a brush, or other device for application to the skin.

Packaging can include single use aliquots in single use packaging such as pouches. The formulation can be packaged in suitable packaging having volumes of about 0.1 oz., about 0.2 oz., about 0.5 oz., about 1 oz., about 2 oz., about 4 oz., about 8 oz., about 16 oz., about 32 oz., about 48 oz., about 64 oz., about 80 oz., about 96 oz., about 112 oz., about 128 oz., about 144 oz., about 160 oz., or an amount within a range defined by any two of the aforementioned values. The packaging can also be squeezable pouches having similar volumes. In some embodiments, packaging may be free of dyes, metal specks, or chemicals that can be dissolved by acids or oxidizing agents. In other embodiments, any bottles, package caps, bottling filters, valves, lines, and heads used in packaging may be specifically rated for acids and oxidizing agents. In some cases, package caps with any organic glues, seals, or other components sensitive to oxidation may be avoided since they could neutralize and weaken the product over time.

As used herein, the term "coadministration" of pharmacologically active compounds refers to the delivery of two or more separate chemical entities or separate therapies, whether in vitro or in vivo. Coadministration refers to the simultaneous delivery of separate agents or therapies; to the simultaneous delivery of a mixture of agents; to the delivery of one agent followed by delivery of a second agent or additional agents; or to the administration of one therapy followed by or concomitant with another therapy. In all cases, agents, agents or therapies that are coadministered are intended to work in conjunction with each other. Similarly, in the context of administration of more than one compound, the term "in combination" refers to a concomitant delivery of one compound with one or more compounds. The compounds may be administered in combination by simultaneous administration or administration of one compound before or after administration of another compound.

In some embodiments, the active ingredients and mixtures of active ingredients can be used, for example, in topical formulations including a pharmaceutically acceptable carrier prepared for storage and subsequent administration. As used herein, "topical" refers to the administration or application of a formulation to the skin or various body orifices. Preservatives can be used to keep the nutrients for the skin cells from breaking down. As used herein, the terms "carrier or diluent" may be a solid carrier or diluent for solid formulations, a liquid carrier or diluent for liquid formulations, or mixtures thereof. Solid carriers/diluents include, but are not limited to, a gum, a starch (e.g., corn starch, pregeletanized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof. For liquid formulations, such as for topical or parenteral formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, almond oil, peanut oil, soybean oil, mineral oil, olive oil, sunflower oil, and fish-liver oil.

The disclosure is generally described herein using affirmative language to describe the numerous embodiments. The disclosure also includes embodiments in which subject matter is excluded, in full or in part, such as substances or materials, method steps and conditions, protocols, or procedures.

Disorders

As provided herein, a topical formulation which may be used in treating a subject in need is provided. The subject in need can have diseases, disorders, ailments, and or damage of skin, hair, and/or nails. In some embodiments, the subject suffers from inflammation. In some embodiments, the subject can have a wound. In some embodiments, the subject suffers from headaches.

"Skin damage" as described herein, can refer to damage to the skin that can be caused by aging, sun damage, cancer, skin disorder or skin diseases that can cause irritation of the skin. Without being limiting, the "skin diseases" and/or "skin disorders" can include rhytide, non-enzymatic glycosylation of the skin, sun damage, smoking damage, fibrosis of the skin, acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriće des jeunes filles, Picker's acne), glandular rosacea, gnathophyma, gram-negative rosacea, granulomatous facial dermatitis, adult male with a large, red, bulbous nose, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus facici, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, skin cancer, tropical acne, psoriasis, including plaque psoriasis, guttate psoriasis, inverse psoriasis, pustular psoriasis, erythrodermic psoriasis, nail psoriasis, psoriatic arthritis, and combinations and/or variations thereof. In some embodiments described herein, a method of treating a subject in need is provided. The subject can have a disease affecting the skin as provided described herein.

"Hair and scalp disorders" are diseases that affect the hair and scalp and are also described herein. Diseases that affect hair and scalp can include but are not limited to alopecia, androgenic alopecia, hirsutism, hair shaft disorders, inflammation, acromegaly, eczema, psoriasis, impetigo, atopic dermatitis, darier discase, and folliculitis. Common causes for scalp disorders can include but are not limited to acromegaly, atopic dermatitis, darier disease, eczema, fragile X syndrome, impetigo, pachydermoperiostosis, psoriasis, and Rosenthal-Kloepfer syndrome. In some embodiments described herein, a method of treating a subject in need is provided. The subject can have a disease affecting the skin and scalp. In some embodiments the subject suffers from alopecia, androgenic alopecia, hirsutism, hair shaft disorders, inflammation, acromegaly, eczema, psoriasis, impetigo, atopic dermatitis, darier disease, and/or folliculitis. In some embodiments, the subject suffers from acromegaly, atopic dermatitis, darier disease, eczema, fragile X syndrome, impetigo, pachydermoperiostosis, psoriasis, and/or Rosenthal-Kloepfer syndrome. In some embodiments, the treating includes administering a formulation to the subject in need. In some embodiments, the formulation is within a hair cream, a hair gel, a scalp lotion, a shampoo, conditioner, hair spray, or a hair mousse.

"Nail diseases" are disorders or diseases that affect the nail, nail bed, or cuticle region and are also described herein. Diseases that affect the nail and surrounding skin area such as the cuticle can lead to infection or inflammation that could require medical assistance. Diseases that infect the nail, nail bed, and/or cuticle can include but is not limited to onychia, onchyocryptosis, onychodystophy, onychogryposis, onycholysis, onychomadesis, onychomycosis, tinea unguium, onychophosis, onychoptosis, onchorrhexis, paronychia, Koilonychia, subungual hematoma, onychomatricoma, nail pemphigus, crythronychia, and melanonychia. In some embodiments described herein, a method of treating a subject in need is provided. The subject can have a disease affecting the nails, nail bed, and/or cuticles. In some embodiments, the subject suffers from onychia, onchyocryptosis, onychodystophy, onychogryposis, onycholysis, onychomadesis, onychomycosis, tinea unguium, onychophosis, onychoptosis, onchorrhexis, paronychia, Koilonychia, subungual hematoma, onychomatricoma, nail pemphigus, erythronychia, and/or melanonychia. In some embodiments, the treating includes administering a formulation to the subject in need. In some embodiments, the formulation is within a skin cream, a lotion, a cuticle cream, or a nail polish.

"Inflammation" as described herein, refers to a biological response of a body tissue to harmful stimuli. The harmful stimuli can include but is not limited to pathogens, bacteria, viruses, fungi, damaged cells, and other irritants that are known to those skilled in the art. Inflammation can be a protective immune response that can involve, for example, immune cells, white blood cells, blood vessels, molecular mediators, and other small molecules. Signs of inflammation can include but is not limited to pain, heat, swelling, and/or loss of function. Inflammation can be acute or chronic. In some embodiments described herein, a formulation is provided for the treatment of inflammation. In some embodiments, the subject suffers from inflammation. In some embodiments, the inflammation is on the skin, scalp, nasal passages, mouth, nail area such as the cuticles, eyes, vaginal area or the perineal area.

Kief Extraction

Kief refers to the resinous trichomes of cannabis that may be sifted from loose, dry cannabis flower. The composition of cannabinoids in kief differs from that of the flowers from which it is derived. For example, kief contains a higher concentration of THC. Extraction may be employed as a technique for separating out some of the components of kief. In some embodiments, the extraction is carried out with an aqueous solvent. In some embodiments, the aqueous solvent is water. In some embodiments, the extraction is carried out with an organic solvent. In some embodiments, the extracting solvent is kept at a temperature of about 0° C. during the extraction.

EXAMPLES

Some aspects of the embodiments discussed above are disclosed in further detail in the following examples, which are not in any way intended to limit the scope of the present disclosure. Those in the art will appreciate that many other embodiments also fall within the scope of the disclosure, as it is described herein above and in the claims.

Example 1. Preparation of Cannabis Flower Cream

The following example describes an embodiment of a topical formulation and the method of making the formulation.

A topical formulation was prepared with the ingredients as provided in Table 1. The chamomile flower, lavender flower, and cannabis flower were combined with the almond oil and allowed to sit. After two hours, the flower solids were removed from the oil by filtration. Two ounces of the resulting oil were then combined with the shea butter, cocoa butter, arnica oil, and tea tree oil. The resulting mixture was subjected to mechanical pulverization.

TABLE 1

Cannabis Flower Cream Formulation

| Ingredient | Amount | Role in Formulation |
| --- | --- | --- |
| Chamomile flower | 20 grams | Plant extract |
| Lavender flower | 20 grams | Plant extract |
| Cannabis flower | 10 grams | Cannabis flower extract |
| Almond oil | 12 ounces | Extracting solvent |
| Shea butter | 1.5 cups | Emollient |
| Cocoa butter | ½ cup | Emollient |
| Arnica oil | 2 tablespoons | Plant extract |
| Tea tree oil | 2 tablespoons | Plant extract |

Example 2. Kief Cream Formulation

The following example describes an embodiment of a topical formulation and the method of making the formulation.

A topical formulation was prepared with the ingredients as provided in Table 2. The kief and almond oil were combined and heated at a temperature of about 260° C. After two to four hours, the mixture was cooled, and the kief solids were removed from the oil by filtration. Two ounces of the resulting oil were then combined with the shea butter, cocoa butter, arnica oil, chamomile, tea tree, and lavender. The resulting mixture was subjected to mechanical pulverization.

TABLE 2

Kief Cream Formulation

| Ingredient | Amount | Role in Formulation |
| --- | --- | --- |
| Kief | 1 ounce | Kief extract |
| Almond oil | 4 ounces | Extracting solvent |
| Shea butter | 1.5 cups | Emollient |
| Cocoa butter | ½ cup | Emollient |
| Arnica oil | 2 tablespoons | Plant extract |
| Chamomile oil | 1 tablespoons | Plant extract |
| Tea tree oil | 4 tablespoons | Plant extract |
| Lavender oil | 4 tablespoons | Plant extract |

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least." the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of making a topical composition comprising:
   a) combining cannabis flower, lavender flower, arnica, and almond oil to create a first mixture;
   b) heating the first mixture to a temperature within a range of about 250° C. to about 300° C. for about two hours to about four hours;
   c) removing solids from the first mixture by filtration to create a filtrate; and
   d) combining the filtrate with shea butter, kokum butter, and mango butter to create a second mixture.

2. The method of claim 1, wherein the first mixture is heated to a temperature of about 260° C.

3. The method of claim 1, wherein the first mixture is heated for about two hours.

4. The method of claim 1, wherein the filtration is carried out with a paper filter.

5. A method of making a topical composition comprising:
   a) combining kief, lavender flower, arnica, and almond oil to create a first mixture;
   b) heating the first mixture to a temperature within a range of about 250° C. to about 300° C. for about two hours to about four hours;
   c) removing solids from the first mixture by filtration to create a filtrate; and
   d) combining the filtrate with shea butter, kokum butter, and mango butter to create a second mixture.

6. The method of claim 5, wherein the first mixture is heated to a temperature of about 260° C.

7. The method of claim 5, wherein the first mixture is heated for about two hours.

8. The method of claim 5, wherein the filtration is carried out with a paper filter.

* * * * *